(12) United States Patent
Machovina et al.

(10) Patent No.: US 11,473,286 B2
(45) Date of Patent: Oct. 18, 2022

(54) FILTRATION ASSEMBLY FOR REDUCING MALAODORS IN AIR AND AEROSOLIZED WASTE FROM TOILETS

(71) Applicant: HOUND TECH LLC, Coral Gables, FL (US)

(72) Inventors: Brian L. Machovina, Coral Gables, FL (US); Eileen McHale-Machovina, Coral Gables, FL (US)

(73) Assignee: HOUND TECH LLC, Coral Gables, FL (US)

( * ) Notice: Subject to any disclaimer, the term of this patent is extended or adjusted under 35 U.S.C. 154(b) by 206 days.

(21) Appl. No.: 16/362,063

(22) Filed: Mar. 22, 2019

(65) Prior Publication Data

US 2019/0218762 A1     Jul. 18, 2019

Related U.S. Application Data

(63) Continuation-in-part of application No. 15/909,344, filed on Mar. 1, 2018, now abandoned.

(Continued)

(51) Int. Cl.
     *E03D 9/052*      (2006.01)
     *B01D 46/00*      (2022.01)
(Continued)

(52) U.S. Cl.
     CPC .............. *E03D 9/052* (2013.01); *A61L 9/20* (2013.01); *B01D 46/0038* (2013.01);
(Continued)

(58) Field of Classification Search
     CPC .... E03D 9/052; B01D 53/02; B01D 46/0038; B01D 53/007; B01D 2253/102;
(Continued)

(56) References Cited

U.S. PATENT DOCUMENTS

| | | |
|---|---|---|
| 2,238,461 A | 4/1941 | Carman |
| 3,386,109 A | 6/1968 | Christian et al. |

(Continued)

FOREIGN PATENT DOCUMENTS

| | | |
|---|---|---|
| CA | 2709045 | 1/2012 |
| DE | 4009162 A1 * | 11/1990 |

(Continued)

OTHER PUBLICATIONS

Daikin Industries, Ltd—"Air Purifier Operational Manual"—Mar. 4, 2011.

(Continued)

*Primary Examiner* — Regina M Yoo
(74) *Attorney, Agent, or Firm* — Malloy & Malloy, P.L.

(57) ABSTRACT

An assembly for filtering toilet bowl odors including a first housing respectively disposed in spaced relation to and in fluid communication with the toilet bowl. A conduit connects interiors of the first and second housings in fluid communication with one another. A fan assembly is mounted within said first housing in fluid communicating relation with second housing, via the conduit, and is disposed and structured to define a path of fluid flow extending from an inlet of said second housing, through said conduit and a filter assembly, disposed in the first housing and/or second housing, to the exterior of said first housing, concurrent to activation of the fan assembly.

12 Claims, 9 Drawing Sheets

Related U.S. Application Data

(60) Provisional application No. 62/726,624, filed on Sep. 4, 2018, provisional application No. 62/465,963, filed on Mar. 2, 2017.

(51) Int. Cl.
  *B01D 53/00* (2006.01)
  *B01D 53/02* (2006.01)
  *A61L 9/20* (2006.01)
  *A61L 9/12* (2006.01)
  *A61L 9/014* (2006.01)

(52) U.S. Cl.
  CPC ........... *B01D 53/007* (2013.01); *B01D 53/02* (2013.01); *A61L 9/014* (2013.01); *A61L 9/12* (2013.01); *A61L 2209/14* (2013.01); *A61L 2209/22* (2013.01); *B01D 2253/102* (2013.01); *B01D 2257/90* (2013.01); *B01D 2258/06* (2013.01); *B01D 2259/804* (2013.01); *B01D 2273/30* (2013.01)

(58) Field of Classification Search
  CPC ............ B01D 2257/90; B01D 2258/06; B01D 2259/804; B01D 2273/30; A61L 9/20; A61L 9/12; A61L 9/014; A61L 2209/14; A61L 2209/22
  See application file for complete search history.

(56) References Cited

U.S. PATENT DOCUMENTS

| | | |
|---|---|---|
| 3,491,382 A | 1/1970 | Poister |
| 3,763,505 A | 10/1973 | Zimmerman |
| 3,849,808 A | 11/1974 | Olson et al. |
| 4,117,559 A | 10/1978 | Boyle |
| 4,375,704 A | 3/1983 | Smith |
| 4,472,841 A | 9/1984 | Faulkner |
| 4,726,078 A | 2/1988 | Carballo et al. |
| 4,876,748 A | 10/1989 | Chun |
| 4,944,045 A * | 7/1990 | Agelatos ................. E03D 9/052 4/213 |
| 5,044,325 A | 9/1991 | Miksitz |
| 5,273,487 A | 12/1993 | Dauvergne |
| 5,333,321 A | 8/1994 | Redford |
| 5,345,617 A | 9/1994 | Jahner et al. |
| 5,454,122 A | 10/1995 | Bergeron |
| 5,564,364 A | 10/1996 | Kovacs et al. |
| 5,671,484 A * | 9/1997 | Lee, III ................... E03D 9/052 4/209 R |
| 5,681,533 A | 11/1997 | Hiromi |
| 5,727,262 A * | 3/1998 | Littlejohn ............... E03D 9/052 4/213 |
| 5,778,822 A | 7/1998 | Giffin et al. |
| 6,003,157 A * | 12/1999 | Bruyere .................. E03D 9/052 15/327.6 |
| 6,233,750 B1 | 5/2001 | Donald et al. |
| 6,260,214 B1 | 7/2001 | Smith |
| 6,279,173 B1 | 8/2001 | Denzin et al. |
| 6,312,507 B1 | 11/2001 | Taylor et al. |
| 6,313,371 B1 | 11/2001 | Conant et al. |
| 6,449,778 B1 | 9/2002 | Franco |
| 6,457,186 B1 | 10/2002 | Stewart |
| 6,494,940 B1 | 12/2002 | Hak |
| 6,546,567 B2 | 4/2003 | Kuzniar |
| 6,588,025 B1 * | 7/2003 | Helmolt ................. E03D 9/052 4/213 |
| 6,610,121 B2 | 8/2003 | Chasen |
| 6,643,850 B2 | 11/2003 | Chasen et al. |
| 6,701,538 B2 | 3/2004 | Hunnicutt, Jr. et al. |
| 6,760,928 B1 | 7/2004 | Rodriguez |
| 6,834,530 B2 | 12/2004 | Kita et al. |
| 6,848,989 B2 | 2/2005 | Miyazaki et al. |
| 7,073,223 B2 | 7/2006 | Huza |
| 7,076,371 B2 | 7/2006 | Fu |
| 7,166,259 B2 | 1/2007 | Beam et al. |
| 7,222,494 B2 | 5/2007 | Peterson et al. |
| 7,326,387 B2 | 2/2008 | Arts et al. |
| 7,347,888 B2 | 3/2008 | Hecker et al. |
| 7,380,292 B1 | 6/2008 | Harris |
| 7,615,109 B2 | 11/2009 | Sepke et al. |
| 7,823,227 B2 | 11/2010 | Damianoe et al. |
| 7,913,332 B1 | 3/2011 | Barnhart |
| 8,083,575 B2 | 12/2011 | Kim et al. |
| 8,161,579 B2 | 4/2012 | Denkewicz, Jr. et al. |
| 8,485,131 B2 | 7/2013 | Veness et al. |
| 8,490,221 B1 | 7/2013 | Conde |
| 8,828,733 B2 | 9/2014 | Porter et al. |
| 9,119,748 B2 | 9/2015 | Abraham et al. |
| 9,266,118 B2 | 2/2016 | Iwaki |
| 9,612,188 B2 | 4/2017 | Johnston et al. |
| 9,889,719 B2 | 2/2018 | Isert et al. |
| 2002/0069456 A1 | 6/2002 | Kuzniar |
| 2002/0189008 A1 | 12/2002 | Hipponsteel |
| 2003/0019019 A1 | 1/2003 | Blanch et al. |
| 2003/0099575 A1 | 5/2003 | Sung et al. |
| 2003/0163863 A1 * | 9/2003 | Stone ...................... E03D 9/052 4/213 |
| 2003/0192112 A1 | 10/2003 | Ware |
| 2006/0031979 A1 | 2/2006 | Johnson |
| 2006/0064803 A1 | 3/2006 | Wang |
| 2006/0064805 A1 | 3/2006 | Yamamoto |
| 2006/0182672 A1 | 8/2006 | Hallam |
| 2006/0195975 A1 | 9/2006 | Kirby |
| 2007/0234469 A1 | 10/2007 | Denkewicz et al. |
| 2007/0256219 A1 | 11/2007 | Ellinger |
| 2008/0000017 A1 * | 1/2008 | Littrell ................... E03D 9/052 4/213 |
| 2008/0060119 A1 | 3/2008 | Pinizzotto |
| 2008/0063558 A1 | 3/2008 | Coleman |
| 2008/0083056 A1 * | 4/2008 | Damianoe ............... E03D 9/052 4/213 |
| 2008/0301865 A1 | 12/2008 | Hand |
| 2009/0056007 A1 | 3/2009 | Pham |
| 2009/0064864 A1 | 3/2009 | Mann et al. |
| 2009/0158515 A1 | 6/2009 | Bruno |
| 2009/0233888 A1 | 9/2009 | Lin |
| 2009/0307831 A1 | 12/2009 | Shahar |
| 2010/0037679 A1 | 2/2010 | Niezgoda et al. |
| 2010/0132624 A1 | 6/2010 | Ferrer et al. |
| 2010/0180830 A1 | 7/2010 | Fritter et al. |
| 2010/0199413 A1 | 8/2010 | Pollack et al. |
| 2010/0235974 A1 | 9/2010 | Reed |
| 2011/0047686 A1 | 3/2011 | Moore |
| 2011/0203040 A1 | 8/2011 | Brown |
| 2012/0042877 A1 | 2/2012 | Wu et al. |
| 2012/0186007 A1 | 7/2012 | Perez |
| 2013/0047858 A1 | 2/2013 | Bohlen et al. |
| 2013/0152790 A1 | 6/2013 | Ingledew et al. |
| 2013/0205484 A1 | 8/2013 | Taciuc |
| 2014/0059750 A1 | 3/2014 | Bochnik |
| 2014/0137317 A1 | 5/2014 | Sollami |
| 2014/0298576 A1 | 10/2014 | Gallardo Chaparro et al. |
| 2014/0331625 A1 | 11/2014 | Gruenbacher et al. |
| 2015/0098860 A1 | 4/2015 | Aldereguia et al. |
| 2016/0223548 A1 | 8/2016 | Kizuka et al. |
| 2016/0245784 A1 | 8/2016 | Matocha et al. |
| 2016/0250370 A1 | 9/2016 | Orito |
| 2016/0286971 A1 | 10/2016 | Pan |
| 2016/0325606 A1 | 11/2016 | Kim |
| 2016/0361677 A1 | 12/2016 | Blackley |
| 2017/0014009 A1 | 1/2017 | Smith |
| 2017/0036516 A1 | 2/2017 | Kim |
| 2017/0107709 A1 | 4/2017 | Kausch et al. |
| 2018/0154297 A1 * | 6/2018 | Maletich ............... B01D 53/047 |
| 2018/0250430 A1 | 9/2018 | Machovina et al. |

FOREIGN PATENT DOCUMENTS

| | | |
|---|---|---|
| EP | 0748902 | 12/1996 |
| EP | 3037594 | 6/2016 |
| JP | 2021536331 | 12/2021 |
| KR | 10-0968504 | 7/2010 |

(56) References Cited

FOREIGN PATENT DOCUMENTS

| WO | WO 2006/041836 | 4/2006 |
|---|---|---|
| WO | WO 2009/130884 | 10/2009 |
| WO | WO 2013/061181 | 5/2013 |
| WO | WO 2015/109406 | 7/2015 |
| WO | WO 2017/104927 | 6/2017 |
| WO | WO 2018/009715 | 1/2018 |
| WO | WO 2018/160835 | 9/2018 |

OTHER PUBLICATIONS

Robert Clain—"ECE 4760: Introduction Microcontroller Programming Final Design Project"—Jan. 1, 2009.
Fuchs et al.—"Evaluation of Unpleasant Odor with a Portable Electronic Nose"—Oct. 17, 2007.
Capelli et al. "Measuring Odours in the Environment vs. Dispersion Modelling: A Review" Jul. 15, 2013.
Moore et al.—"Gas-Chromatographic and Mass-Spectrometric Analysis of the Odor of Human Feces"—Jan. 1, 1987.
Ortiz Perez et al. "Low-Power Odor-Sensing Network Based on Wake-Up Node"—Aug. 25, 2017.
Qu G. et al.—"Development of an Integrated Sensor to Measure Odors"—Sep. 1, 2008.
Yoon et al.—"A Study of Odor Emission Characteristics from Human Waste/Livestock Manure Treatment Facilities in Korea"—Aug. 20, 2014.
Kwiatkowska-Stenzel et al.—"Analysis of Noxious Gas Pollution in Horae Stable Air"—Jul. 29, 2013.
Pandey et al.—"Human Body-Odor Components and Their Determination"—Jan. 1, 2011.
Schiffman et al.—"Dispersion Modeling to Compare Alternative Technologies for Odor Remediation at Swine Facilities"—Sep. 1, 2008.
Pan et al.—"A New Intelligent Electronic Nose System for Measuring and Analysing Livestock and Poultry Farm Odours"—Dec. 1, 2007.
Capelli et al.—"Electronic Noses for Environmental Monitoring Applications"—Oct. 24, 2014.
Lim et al.—"Odor and Gas Release from Anaerobic Treatment Lagoons for Swine Manure"—Mar. 1, 2003.
Ortiz Perez et al. "Odor-Sensing System to Support Social Participation of People Suffering from Incontinence"—Jan. 1, 2007.
Mackie et al.—"Biochemical Identification and Biological Origin of Key Odor Components in Livestock Waste"—Jun. 1, 1998.

* cited by examiner

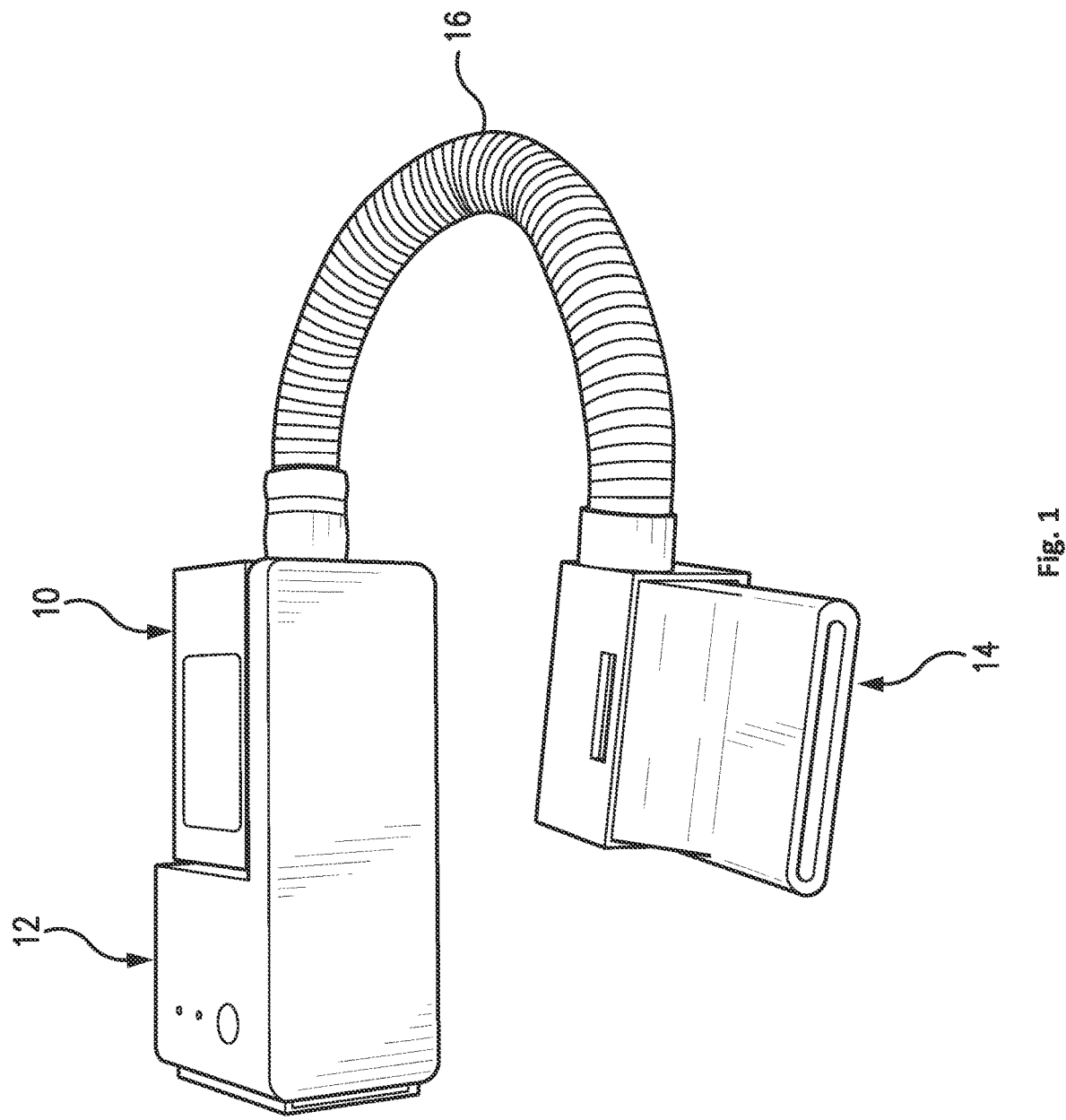

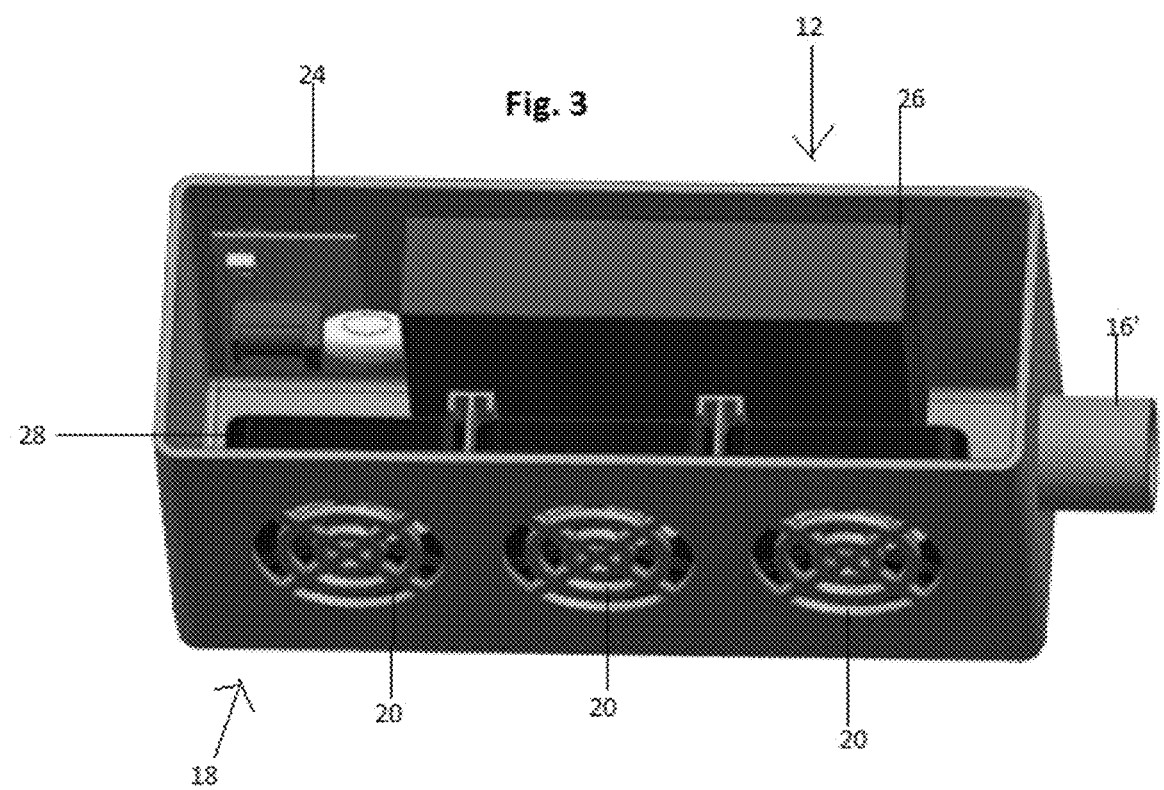

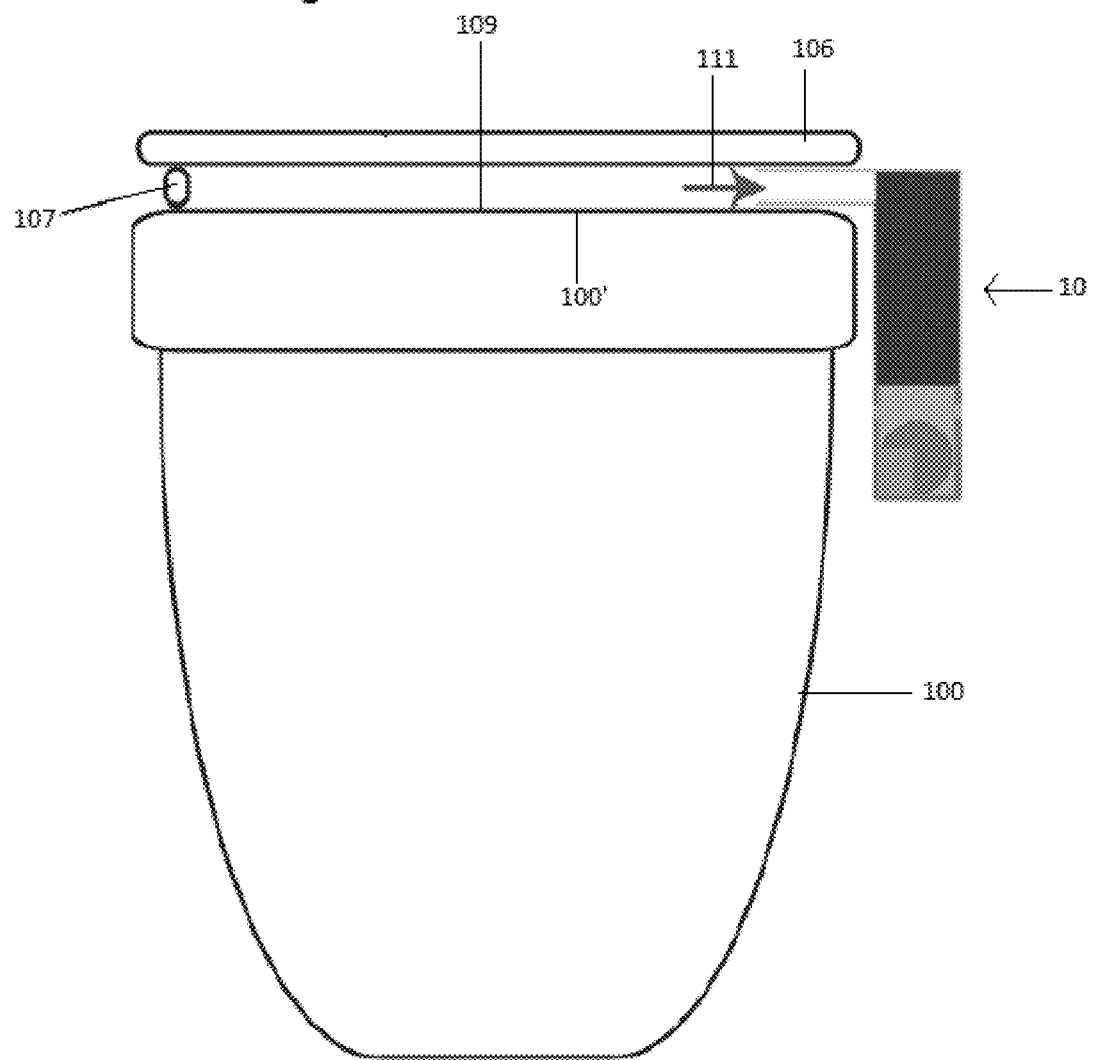

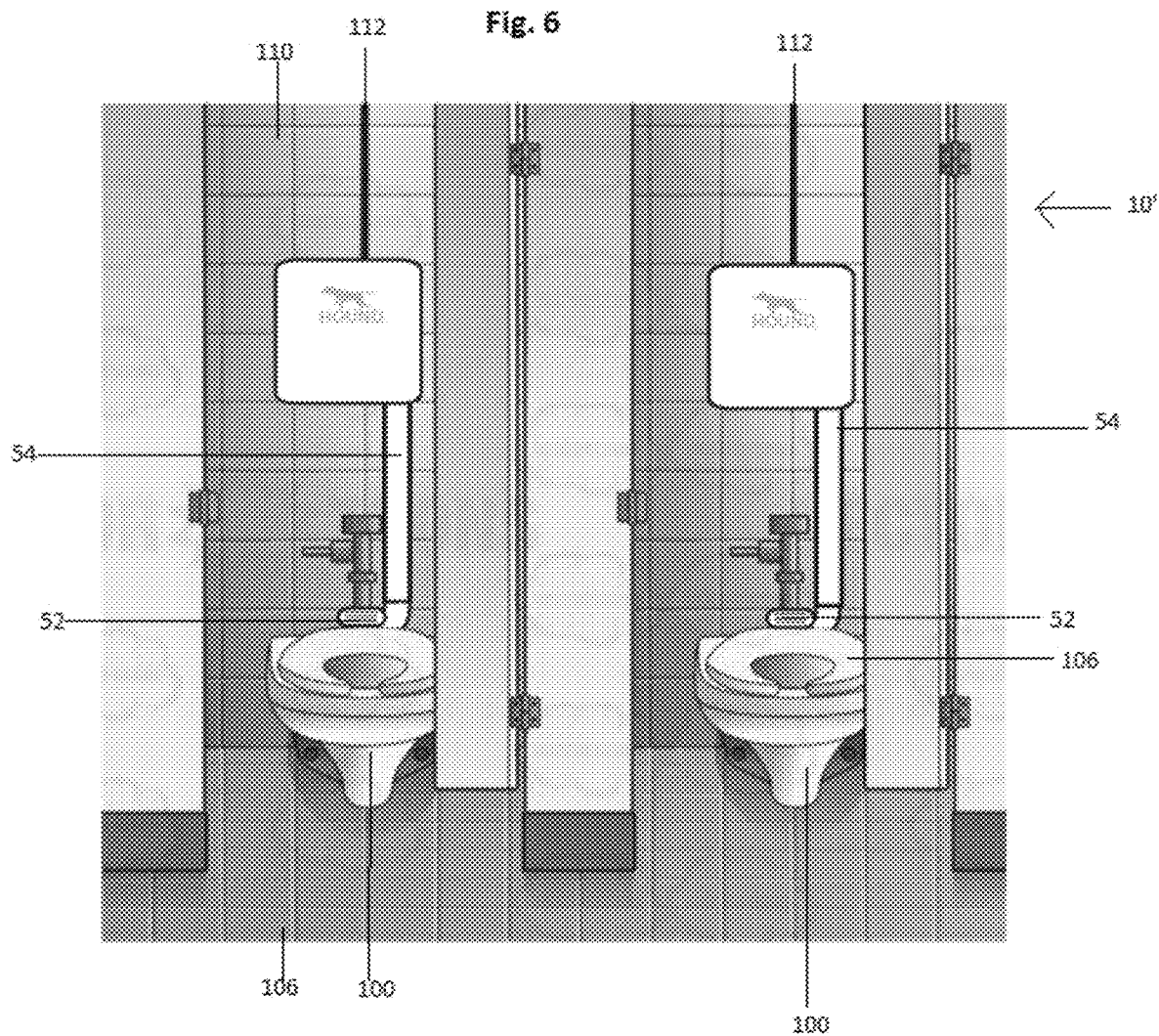

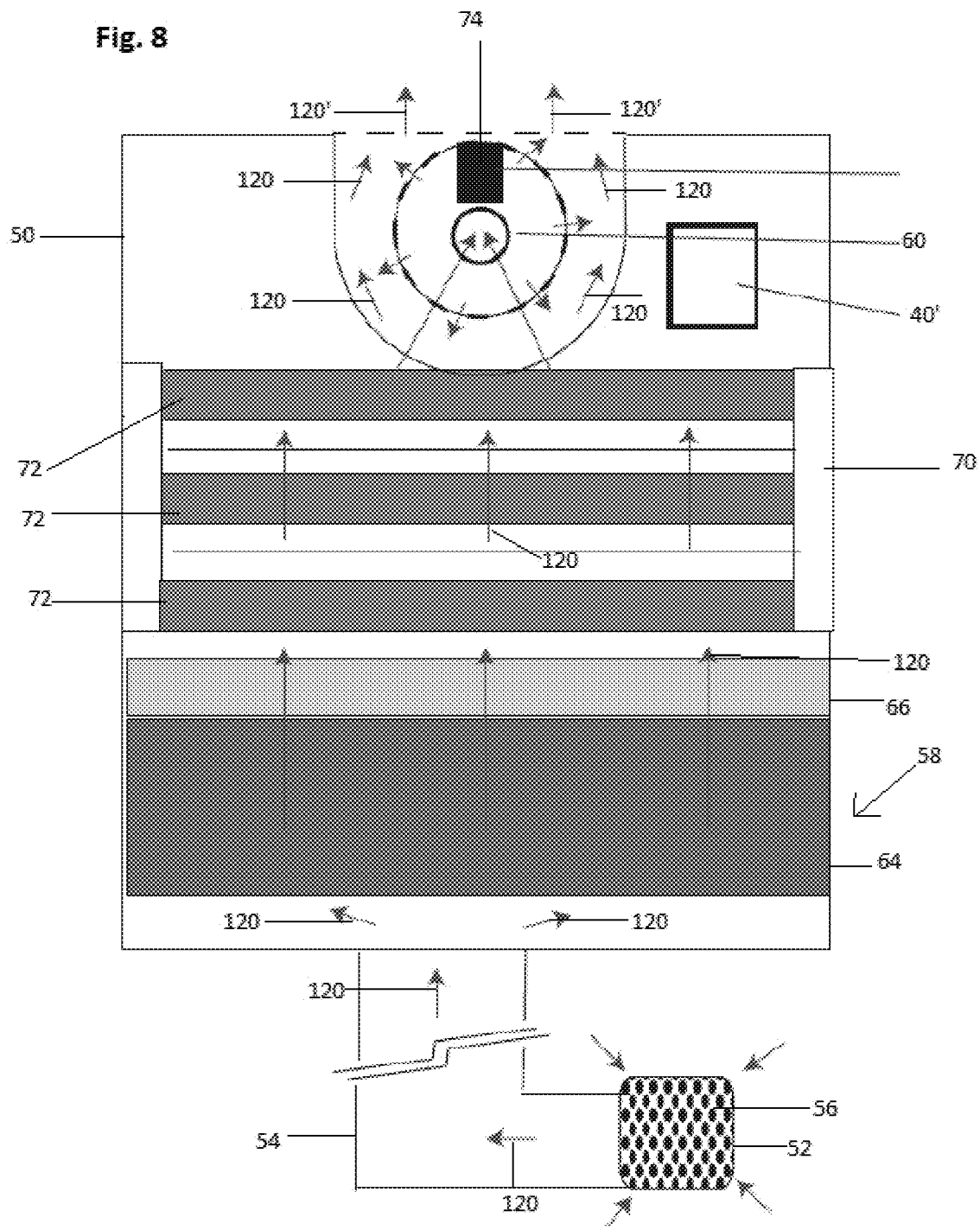

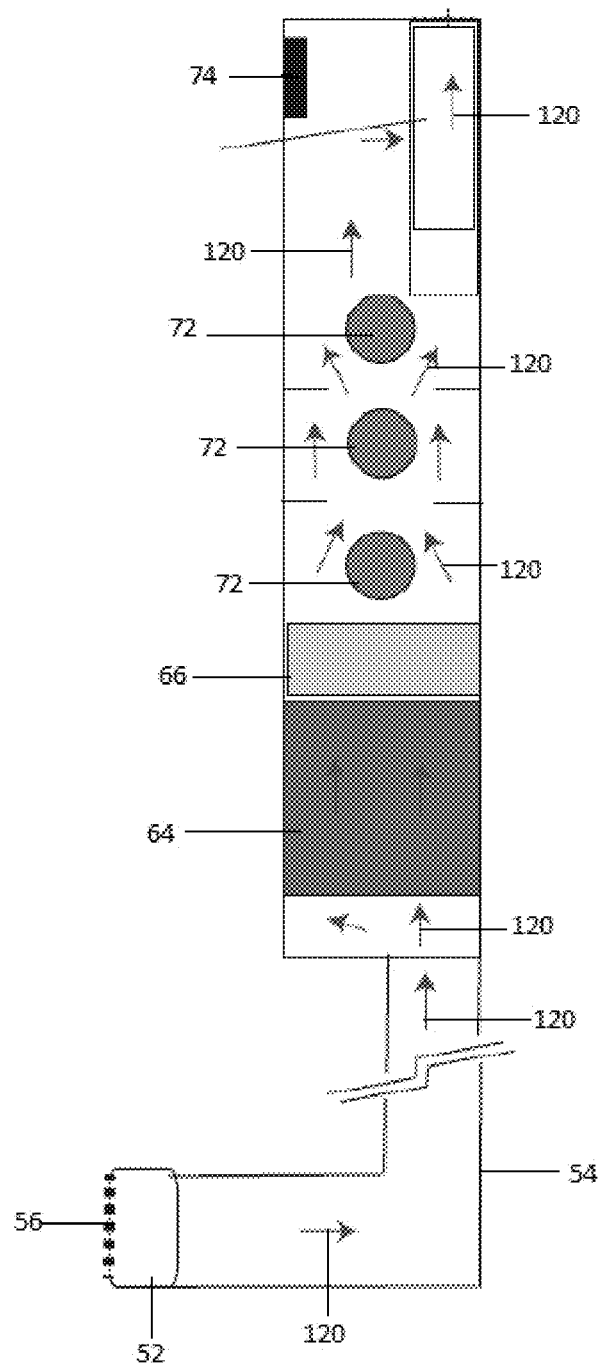

FILTRATION ASSEMBLY FOR REDUCING MALAODORS IN AIR AND AEROSOLIZED WASTE FROM TOILETS

The present application is a Continuation-In-Part application of previously filed, now application having U.S. application Ser. No. 15/909,344, which was filed on Mar. 1, 2018, to which a claim of priority is made under 35 U.S.C. Section 119(e) to a provisional patent application having U.S. Application No. 62/465,963, which was filed on Mar. 2, 2017, and which are incorporated herein by reference.

A further claim of priority is made under 35 U.S.C. Section 119(e) to a provisional patent application that in the U.S. Patent and Trademark Office, namely, that having U.S. Application No. 62/726,624, which was filed on Sep. 4, 2018, and which is incorporated herein by reference.

BACKGROUND OF THE INVENTION

Field of the Invention

This invention is directed to an assembly for the filtration and other processing of air and aerosolized fluid issuing from the interior of a toilet bowl.

Description of the Related Art

The odor of human waste released by people into a toilet bowl can enter the general surrounding area and remain suspended during toilet use and for periods of time post toilet use. This can be unpleasant to the present toilet user, to others located in the nearby environment, or to others that enter the area later to use the same toilet.

Air purifiers and air filters are widely used in interior spaces such as homes and offices to minimize the amount of dust, allergens, and micro-organisms that are present in the air. These systems typically include a fan for circulating air and a mechanical filter disposed in an air path to filter or purify air flowing there through. Larger fans, air purifiers and/or air filters tend to be more effective due to the large volume of air they can remove, filter and/or purify at a given time. However, larger units of this type are usually obtrusive and take up a considerable amount of space in the home or office. Further, these larger systems may require more electricity and are often loud due to the size of the fans included in the system.

Although fans, air purifiers and air filters may provide a solution to combating the presence of contaminants such as dust, allergens and micro-organisms, they may lack the means to effectively remove the odors from the air. Individuals are well aware of the offensive odors that may be released from flatulence, feces, or urine. These odors can be disruptive and unpleasant to individuals located in the vicinity of such odors. When unpleasant odors are present in the air, individuals usually commonly use air freshener sprays, plug in air fresheners or the like, to "cover-up" the unpleasant odor with a more pleasant scent. However, this tactic merely masks the presence of the unpleasant odor and does nothing to actually remove the odor.

Additionally, the use of air fresheners or sprays presents an unfortunate problem because an individual must first come in contact with the unpleasant odor before these devices can be used to mask the scent. Furthermore, while the scent of air fresheners, sprays, etc. may provide a more pleasant odor, as compared to odors released from flatulence, feces or urine, some individuals may not enjoy still not enjoy or even be able to tolerate such fragrances.

Accordingly, there is a need for an air filter and/or odor processing assembly and/or system operative to withdraw, filter and otherwise treat or process odors, specifically including those emanating from flatulence, defecation and/or urination, directly from a toilet bowl airspace. Treatment of such odors thereby eliminate or significantly reduce the release thereof into the surrounding airspace. Such processing and/or treatment of such odors may include passing air or aerosolized fluid containing such odors across a filter assembly operatively structured to absorb the odors. In addition, a proposed assembly and/or system of the type referred to may also include a filter assembly capable of removing aerosolized particles contained in a "toilet plume".

Moreover, the treatment or processing of fluid removed from the interior of a toilet bowl may also include sterilizing capabilities operative to remove germs, bacteria, etc. prior to reaching the air or space surrounding the toilet. In addition, modification of certain structural and operative features may serve to enhance the versatility of an improved odor elimination assembly and/or system, thereby enabling its use in both domestic and commercial environments. Finally, a proposed and improved toilet odor processing assembly and or system which overcomes known disadvantages of the type set forth above, should be designed to be inexpensive, easily serviceable and convenient enough to change install and maintain.

SUMMARY OF THE INVENTION

The present invention is directed to an assembly for filtering/removing odors issuing from a toilet bowl. In addition, one or more preferred embodiments of the filter assembly is operative to filter/remove odors from air as well as processing aerosolized fluid, resulting from a "toilet plume" which may develop when the toilet is flushed. As will be explained in greater detail hereinafter, different ones of a possible plurality of embodiments of the filtering assembly may be structurally and operatively adapted for use in either a domestic environment or commercial environment and/or both.

Accordingly, at least one preferred embodiment of the present invention comprises a first housing disposed in spaced relation to the toilet bowl and having a fan assembly disposed therein. A second housing is disposed in adjacent relation to the toilet bowl and includes an inlet disposed in fluid communication with the toilet bowl interior. The second housing includes a filter segment and a connector segment removably connected to one another, wherein a filter is fixedly disposed and retained within the filter segment. Moreover, the fixedly retained filter is disposed adjacent to and/or otherwise downstream of the inlet, in receiving relation to fluid passing into the interior of the filter segment of the second housing through the inlet.

An elongated conduit is disposed in interconnecting, fluid communicating relation between interiors of the first and second housings. The elongated conduit is disposed and structured to direct the flow of fluid entering the second housing through the inlet and retained filter in the filter segment, through the interior of the connecting segment and along the length of the conduit into first housing. Accordingly, a path of fluid flow is established from the inlet, through the filter in the filter segment of the second housing, through the connector segment, along the length of the conduit and into and through the interior of the first housing, concurrent to activation of the aforementioned fan assembly, within the first housing.

Further, the fan assembly is disposed and structured, when activated, to direct fluid flow from the interior of the first housing outwardly therefrom to an exterior thereof. As a result, air/fluid passing into the second housing, through the aforementioned inlet will be sufficiently processed, at least in terms of removing or significantly eliminating odor contained therein, for subsequent entry back into the space or area surrounding the toilet.

Additional structural and operative features of at least one embodiment of the filtering assembly includes the aforementioned fan assembly, being disposed in the first housing and comprising at least one or in the alternative a plurality of fan units. As such, when activated, the one or more fan units are individually and/or collectively disposed to direct fluid flow along the path of travel from the interior of the second housing, through the conduit, and through and outwardly from the interior of the first housing.

As indicated, the filter segment and the connector segment collectively and at least partially defining the second housing are removably connected to one another, such that the interiors thereof are in direct fluid communication. The removable connection therebetween preferably comprises, but is not limited to, an inner end of both the filter segment and connector segment being cooperatively structured to accomplish removable attachment to one another. Moreover, in at least one embodiment cooperative structural features of the inner ends of the filter and connector segments of the second housing facilitate a telescopic connection therebetween as well as a "snap-fit" attachment. This enables a quick and easy detachment from one another.

In association therewith, another practical advantage of this embodiment of the filter assembly includes the filter segment and the fixedly retained filter therein being collectively detached from the connector segment and structured for disposal after a predetermined period of use. A new filter segment and enclosed filter may then the connected to the existing and/or same connector segment for continued and prolonged use of the remainder of the filter assembly.

In order to facilitate packaging, shipping, installation and maintenance of the filter assembly, the elongated conduit may be removably attached to both the first housing and to the second housing, the latter via the connector segment.

Yet additional features may include the inclusion of a secondary filter disposed within the interior of the first housing and further positioned upstream of the fluid entering the first housing through the conduit and downstream of the fan assembly. As a result, additional filtering of the fluid passing into the inlet of the filter segment of the second housing and therefrom along the conduit into the first housing will be additionally filtered to further facilitate removal of odor. A scent releasing structure or device may also be included, preferably, but not necessarily, within the first housing.

The above noted embodiment of the filter assembly for home use, in a domestic environment, may include a manual on/off user interface. Such interface may be preferably disposed in an exposed location on the exterior of the first housing. Further control circuitry may be contained in the first housing, in the form of a printed circuit board or other appropriate control circuitry. Further, the control circuitry may include time delay capabilities facilitating the automatic turnoff of the fan assembly after the expiration of a predetermined period of time from its manual activation. In the alternative and or in addition thereto the manual on/off user interface may be manipulated to extend the activation of the fan assembly or to cease activation thereof before the predetermined time period has elapsed. In cooperation therewith, this embodiment may preferably be operated by and appropriately powered battery pack, in order to facilitate quick and easy installation, maintenance, etc.

One or more additional embodiments of the filter assembly of the present invention may be structurally and operatively similar to the above described embodiment, but may be more adapted for use in a commercial environment. As such, the additional one or more embodiments of the filter assembly includes a first housing disposed in spaced relation to the toilet bowl and including a filter assembly contained therein. A second housing is disposed adjacent the toilet bowl and includes an inlet disposed in fluid communicating relation with the interior of the toilet bowl. An elongated conduit may be disposed in interconnecting, fluid communicating relation between the interiors of the first and second housings.

Further, a fan assembly is mounted within the first housing in fluid communication with the conduit and through the conduit, in fluid communication with the interior of the second housing and the inlet associated therewith. Therefore, the fan assembly is disposed and structured to direct fluid flow from the conduit through the interior of the first housing and outwardly therefrom to an exterior of the first housing, subsequent to being processed. Accordingly, an activation of the aforementioned fan assembly, within the interior of the first housing, defines or establishes a path of fluid flow extending from said inlet of the second housing, through the conduit and into the interior of the first housing, through the filter assembly, to the exterior of the first housing and back into the space, area or environment surrounding the toilet.

Yet additional features of the additional one or more embodiments of the filter assembly, which may render it more adaptable for use in a commercial environment, comprises the filter assembly including a first filter unit and a second filter unit, both located upstream of the conduit and downstream of the fan assembly. The first filter unit may be a carbon-based filter primarily operative to remove odors from air/gas passing there through. The second filter unit of the filter assembly is preferably structured to process aerosolized fluid and any particulate matter contained therein and may be comprise an HEPA filter. As indicated, aerosolized fluid may result from the toilet being flushed and the creation of a "toilet plume", possibly containing odor causing particulate waste material.

In addition to the filter assembly including, the first and second filter units, a fluid sterilizing assembly may be disposed within the first housing, upstream of the conduit and downstream of the fan assembly. The sterilizing assembly may comprise at least one or in the alternative a plurality of ultraviolet (UV) lights disposed in the path of fluid flow exiting from the aforementioned filter assembly, or otherwise passing through the interior of the first housing.

Possible installation and use of this additional embodiment of the filter assembly of the present invention may include the inclusion of a sensor assembly such as, but not limited to a motion sensor. The sensor assembly may be preferably mounted on the first housing and be positioned/oriented to detect the presence of an individual utilizing the toilet. The sensor assembly may be further structured to activate the fan assembly while an individual remains in a predetermined detection zone. Automatic shutoff of the fan assembly will result upon an absence of an individual from the aforementioned detection zone. Powering of the fan assembly may best be accomplished by a direct wired connection to a conventional AC power source typically associated with most commercial locations which include restrooms and or semi-public toilet facilities.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a perspective view of one embodiment of the assembly of the present invention in an assembled form.

FIG. 3 is a perspective interior view of a first housing of the embodiment of the assembly as represented in FIG. 1.

FIG. 5 is a front elevational view in schematic form of one operative position of the embodiment of FIGS. 4A-4C.

FIG. 6 is a perspective view of yet another embodiment of the assembly of the present invention operatively positioned at different toilet structures.

FIG. 8 is an interior view in schematic form of the embodiment of the assembly as represented in FIG. 6.

FIG. 9 is a longitudinal sectional view of the interior of the schematic representation of the embodiment of FIG. 8.

Like reference numerals refer to like parts throughout the several views of the drawings.

DETAILED DESCRIPTION OF THE PREFERRED EMBODIMENT

Figure 2A:
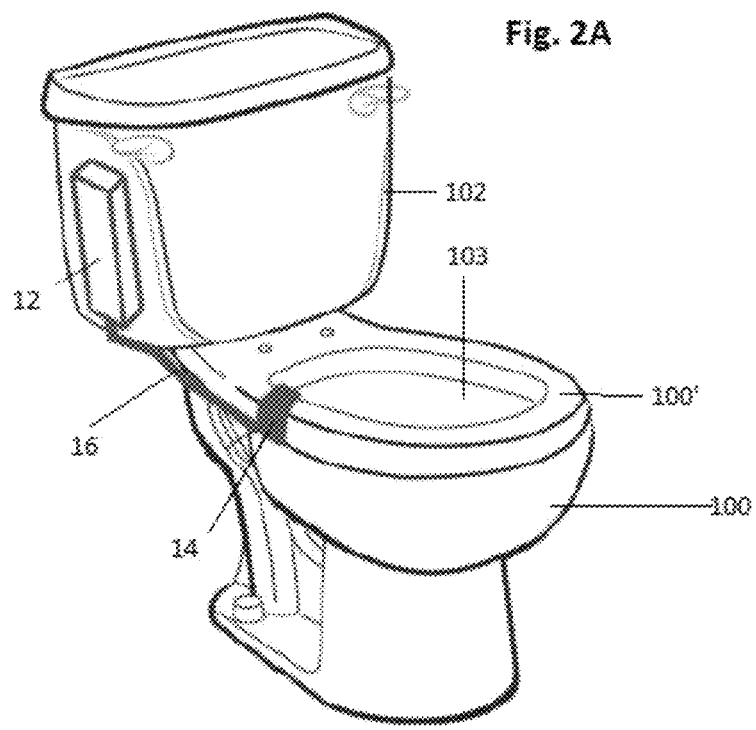
FIG. 2A is a schematic representation of the assembly of the embodiment of FIG. 1 in one operative position.

The present invention is directed to an assembly for filtering odors issuing from a toilet bowl, including one or more embodiments which are operative to filter/remove odors from air and/or aerosolized fluid or "toilet plume", resulting from the toilet being flushed. As described hereinafter in greater detail, different ones of a possible plurality of embodiments of the filtering assembly may be structurally and operatively adapted for use in either a domestic environment or commercial environment and/or both.

Therefore, with primary reference to FIGS. 1-5 at least one preferred embodiment of the filtering assembly is generally indicated as 10 and comprises a first housing 12 and a second housing 14. As schematically represented in FIGS. 2A-2B, the first housing 12 is disposed in spaced relation to the toilet bowl 100, such as being mounted on the water tank 102 operatively associated with the toilet bowl 100. In addition, the second housing 14 is adapted to be removably mounted and/or supported on an outer peripheral rim 100' of the toilet bowl 100 in immediately adjacent, fluid communicating relation with the interior 103 of the toilet bowl 100. The operative positioning of the second housing 14 may vary, such as being mounted on a side portion of the toilet bowl 100, as represented in FIG. 2A and/or on a rear portion of the toilet bowl 100, substantially adjacent the connecting area 105 of a toilet seat 106 (see FIG. 5), as represented in FIG. 2B.

Figure 2B:
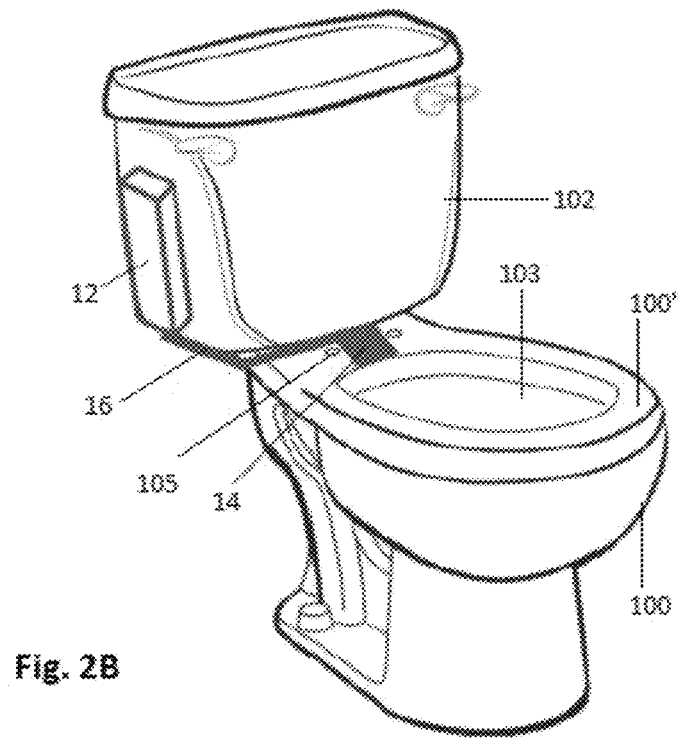
FIG. 2B is a schematic representation of the assembly of the embodiment of FIG. 1 in a different operative position from that represented in FIG. 2A.

The filtering assembly 10 further includes an elongated, preferably flexible material conduit 16 disposed in interconnecting, fluid communicating relation with the interiors of both the first housing 12 and the second housing 14. As demonstrated, the length and flexibility of the conduit 16 may also vary so as to facilitate selective dispositioning and mounting of the second housing 14 in different operative locations on the outer/upper periphery 100' of the toilet bowl 100, as represented in FIGS. 2A-2B. In order to facilitate shipping, storage, installation, maintenance, etc. of the filtering assembly 10, the conduit 16 is removably connected to both the first and second housing 12 and 14 respectively.

Also, the first and second housings 12 and 14 may be removably but securely disposed in different operative positions on the toilet bowl 100 and water tank 102 utilizing an adhesive, or other appropriate connecting structure. Such an adhesive or other connecting structure is preferably disposed on or directly associated with under or rear surface portions of the first and second housings 12 and 14, which engage the water tank 102 and toilet bowl periphery 100', respectively.

With primary reference to FIG. 3, structural and operative features of the first housing 12 includes an at least partially hollow interior appropriately dimensioned to enclose a plurality of operative components. More specifically, the first housing 12 includes a fan assembly generally indicated as 18 comprising at least one but alternatively a plurality of fan units 20. As represented, the one or more fan units 20 are operatively disposed to direct fluid from the interior of the first housing 12 and conduit 16 outwardly to an exterior of the first housing 12 into the area or space surrounding the toilet 100. As indicated, the conduit 16 is removably connected to the first housing 12 by an appropriate fitting 16', such that the interior the conduit 16 is disposed in direct fluid communication with the interior the first housing 12.

Additional structural components within the first housing 12 includes control circuitry generally indicated as 24 which may be in the form of a printed circuit board or other appropriate circuitry, which in turn may be powered by a battery 26 or in the alternative by an AC power source (not shown). Because of the structural and operative versatility of the filtering assembly 10 including, but not limited to, it being battery-powered as well as its ease-of-use, installation, maintenance, etc., as set forth above, the filtering assembly 10 may be suited for use in a home and/or domestic environment.

Also, in order to assure an adequate and effective filtering of fluid passing from the interior of the toilet bowl 100 through the filtering assembly 10, the first housing 12 may also include a secondary filter 22 to be used in conjunction with a primary filter 36, both of which may be activated carbon, associated with the second housing 14, as explained in greater detail hereinafter.

Figure 4A:
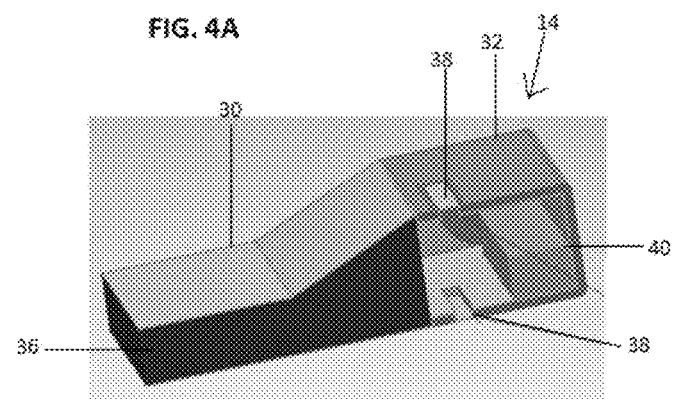
FIG. 4A is an exterior perspective view of a second housing of the embodiment of the assembly as represented in FIG. 1
Figure 4B:
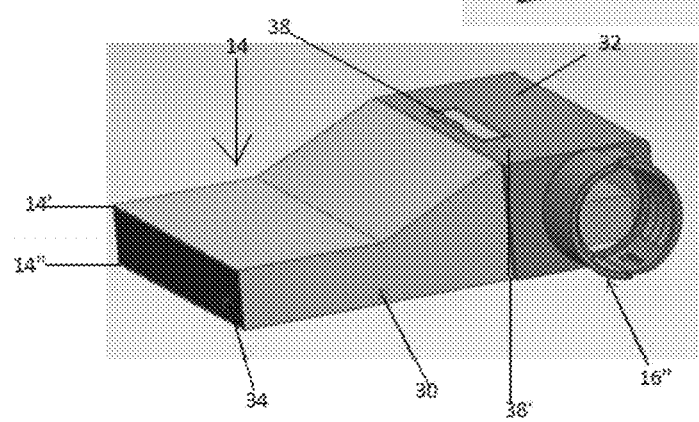
FIG. 4B is a longitudinal sectional view in perspective of the interior of the embodiment of FIG. 4A.
Figure 4C:
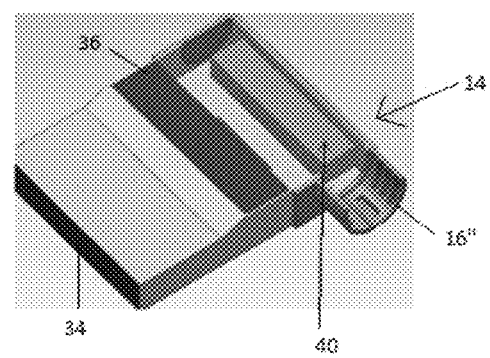
FIG. 4C is a transverse sectional view in perspective of the interior of the embodiment of FIGS. 4A and 4B.

Accordingly, as primarily represented in FIGS. 4A-4C, the second housing 14 comprises a filter segment 30 and a connector segment 32 removably connected to one another such that the interiors thereof are disposed in direct fluid communication with one another. In addition, the filter segment 30 includes an air/fluid inlet 34 formed at and at least partially defining an outer end of the filter segment 30. Also, a primary filter structure 36 is fixedly disposed within the interior of the filter segment 30 in direct fluid communication with fluid passing into the interior of the filter segment 30 through the inlet 34.

The connector segment 32 includes an appropriate fitting as at 16" which facilitates a removable connection to a corresponding end of the conduit 16. As such, when the filter assembly 10 is assembled as represented in at least FIGS. 1 and 2A-2B, the interior of the elongated conduit 16 is disposed in direct fluid communication with the interior of the second housing 14 including the interiors of both the removably connected filter segment 30 and the connector segment 32 and the interior of the first housing 12.

Further, the removable connection between the filter segment 30 and the connector segment 32 of the second housing 14 may be defined by a substantially telescopic and/or snap-fit connection as represented in both FIGS. 4A-4B. As such, the inner end of the filter segment 14 may be at least partially flexible so as to at least partially pass into the interior of the open inner end 32' of the connector segment 32. Further, the inner end of the filter segment 30 includes fixation ribs or like structures 38 disposed, dimensioned and configured to be removably received within a correspondingly disposed apertures or recesses 38' formed adjacent the inner end 32' of the connector segment 32. The flexibility of at least the inner end portion of the filter segment 14 will result in the one or more fixation ribs 38 being "snap-fit" into the correspondingly disposed one or more recesses 38'.

The removable connection of the filter segment 30 from the connector segment 32 facilitates the connector segment 14 and the filter 36 contained therein being accurately described as a replaceable, "single-use" filter medium. More specifically, after a predetermined period of use, the filter 36 may require replacement in order to efficiently operate. Replacement of the filter 36 is accomplished by removal of the second housing 14 from its operative position (see FIGS. 2A-2B) and the subsequent detachment of the filter segment 30 from the connector segment 32. Once detached, the filter segment 30 and the filter 36 fixedly retain therein are collectively structured for disposal. Thereafter, a new or replacement filter segment 30 and fixedly retained filter 36 may be reattached to the connector segment 32 for continued use of the filter assembly 10, once the second housing 14 is disposed in the intended operative position.

Accordingly, once completely assembled and disposed in the intended operative position as represented in FIG. 2A or FIG. 2B, a path of fluid flow is defined and/or established from the inlet 34 of the filter segment 30 of the second housing 14 through the filter 36, the interior of the connector segment 32, along the length of the interior of the conduit 16, into and through the first housing 12, through the secondary filter 28 and out of the first housing 12, through the fan assembly 18, comprising the one or more fan units 20.

Additive features of the filter assembly 10 may comprise the inclusion of additional fragrance or scent materials 40 disposed in one or both the first and second housings 12 and 14 as clearly represented in at least FIGS. 4B and 4C.

In order to assure proper operative placement of the second housing 14 in direct, fluid communicating relation with the interior 103 of the toilet bowl 100, an outer end 14' of the filter segment 14 is appropriately dimensioned and configured to fit within a clearance space 109, beneath a closed seat 106 associated with the toilet bowl 100, as schematically represented in FIG. 5. For purposes of clarity the filter assembly 10, specifically including the second housing 14, is not accurately oriented in order to properly represent the spacing 109 between the toilet seat 106 and the upper or outer periphery 100'.

As commonly structured and utilized, the toilet seat 106 in spaced above the periphery 100' due to the provision of the one or more bumpers 107, typically attached to the undersurface of the toilet seat 106. In cooperation therewith and with reference to FIG. 4A the outer end 14' of the filter segment 14 in the area contiguous and/or adjacent to the inlet 34 has a reduced "height" 14", preferably in the range of generally about 13 mm. As such the reduced height of the outer end 14' of the filter segment 14 is sufficiently dimensioned and configured to fit within the space 109 between the toilet seat 106 and the outer periphery 100', in direct fluid communication with the interior 103 of the toilet bowl 100, as schematically represented by directional arrow 111.

As represented in FIGS. 6-9, one or more additional embodiments of the present invention may include a filter assembly 10', structurally and operatively similar to the above described embodiment of the filter assembly 10, but may be more adapted for use in a commercial environment, as represented in FIG. 6. As such, the at least one additional embodiment of the present invention includes the filter assembly 10' having a first housing 50 disposed in spaced relation to the toilet bowl 100 and also in spaced relation to a second housing 52. When in a commercial environment, the first housing 50 may be mounted on an exposed surface of a wall 110 adjacent to the toilet bowl 100. Further, because of its operative disposition in a commercial environment the filtering assembly 10' may be powered by a conventional AC power supply via a wired connection 112. As also represented in FIG. 6, the filtering assembly 10' includes an elongated conduit 54 disposed in interconnecting, fluid communicating relation between the interiors of the first housing 50 and the second housing 52. As such, the elongated conduit 54 may be operatively similar to the conduit 16 of the above described filtering assembly 10.

Figure 7:
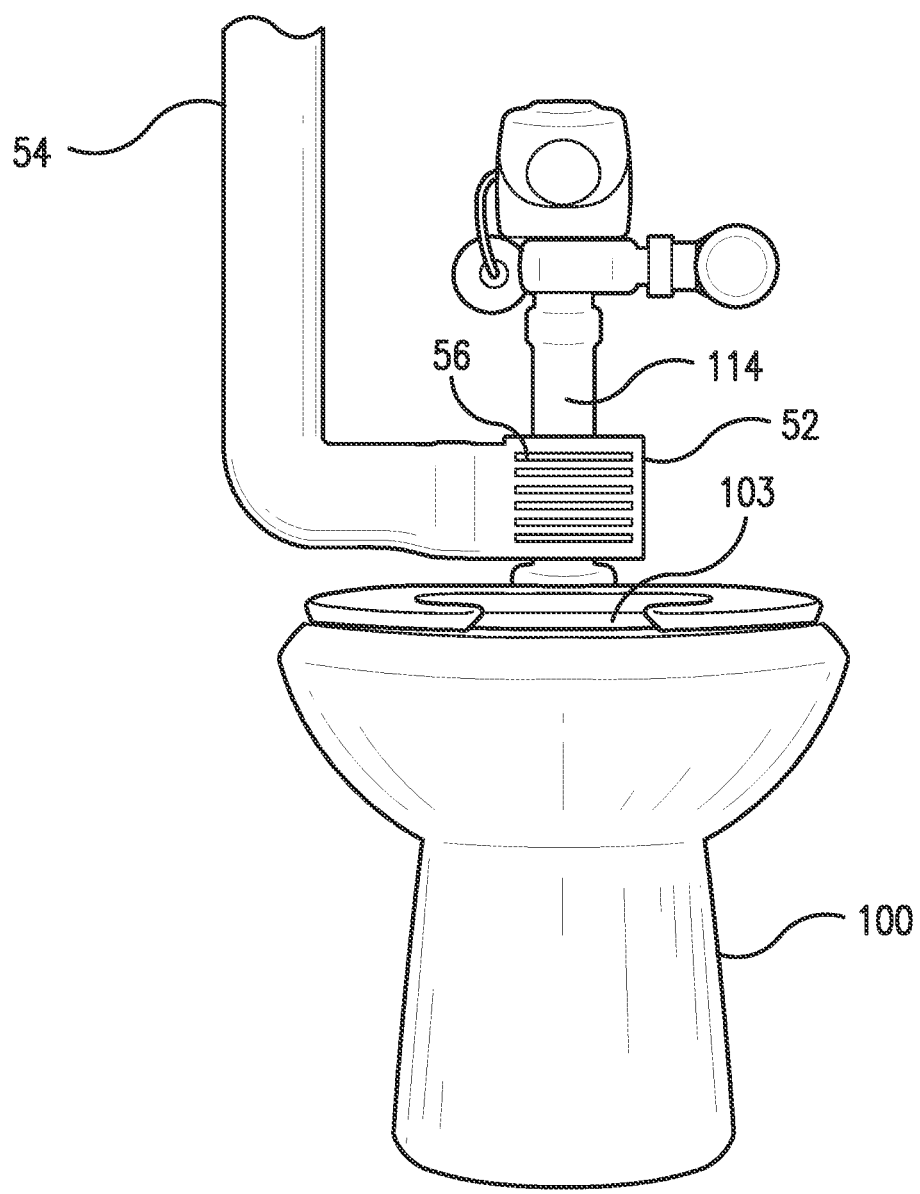
FIG. 7 is a front perspective view in partial cutaway of a portion of the embodiment of the assembly as represented in FIG. 6.

With primary reference to FIG. 7, the second housing 52 includes an inlet 56 operatively disposed immediately adjacent an interior 103 of the toilet bowl 100, such that the inlet 56 is in fluid receiving, fluid communicating relation with the interior 103 of the toilet bowl 100. In order to provide stability, the second housing 52 may be connected to or otherwise supported by a water pipe and/or plumbing fixture 114 associated with the toilet bowl 100 and operative to facilitate the flushing thereof.

As represented in FIGS. 8 and 9, the first housing 50 includes a filter assembly generally indicated as 58, contained therein. In addition, a fan assembly generally indicated as 60 is mounted within the first housing 50 in fluid communication with the conduit 54 and through the conduit 54, in fluid communication with the interior of the second housing 52 and the inlet 56 associated therewith. Therefore, the fan assembly 60, when activated, is disposed and structured to direct fluid flow 120 exiting the conduit 54, through the interior of the first housing 50 and outwardly therefrom to an exterior of the first housing 50, as schematically represented by directional arrows 120', subsequent to being filtered by filter assembly 58. Accordingly, an activation of the fan assembly 60, within the interior of the first housing 50, defines or establishes a path of fluid flow 120 extending from said inlet 56 of the second housing 52, through the conduit 54 and into the interior of the first housing 50, through the filter assembly 58, to the exterior of the first housing 50 and back into the space, area or environment surrounding the toilet bowl 100.

Yet additional features of the additional one or more embodiments of the filter assembly 10', which may render it more adaptable for use in a commercial environment, comprise the filter assembly 58 including a first filter unit 64 and a second filter unit 66, both located in the path of fluid flow 120, downstream of the conduit 54 and upstream of the fan assembly 60. The first filter unit 64 may be a carbon-based and/or carbon activated filter, primarily operative to remove odors from air/gas passing there through. The second filter unit 66 of the filter assembly 58 is preferably structured to process aerosolized fluid and any particulate matter contained therein. As such the second filter unit 66 may comprise an HEPA filter. As indicated, aerosolized fluid may result from the toilet being flushed and the creation of a "toilet plume", possibly containing odor causing particulate waste material.

It is also noted and recognized that the inlet 56 of the second housing 52 is disposed immediately adjacent and preferably exteriorly of the interior 103 of the toilet bowl 100. Accordingly, the fan assembly 60 is adequately powered and otherwise structured to expose the interior 103 of the toilet bowl 100 to a sufficiently strong fluid flow, to "draw" and/or collect aerosolized fluid along the path of fluid flow 120, from the interior 103 of the toilet bowl 100, through the inlet 56 and through the conduit 54, into the interior of the first housing 50, through the filter assembly 58 and outwardly from the exterior of the first housing 50.

In addition to the filter assembly 58 including, the first and second filter units 64 and 66 respectively, a fluid sterilizing assembly 70 may be disposed along the path of fluid flow 120, within the first housing 50, upstream of the conduit 54 and downstream of the fan assembly 60. The sterilizing assembly 70 may comprise at least one or in the alternative a plurality of ultraviolet (UV) lights 72 disposed in the aforementioned path of fluid flow 120 exiting from the filter assembly 58, or otherwise passing through the interior of the first housing 50.

Possible installation and use of this additional embodiment of the filter assembly 10' of the present invention may include a sensor assembly 74 such as, but not limited to, a motion sensor. The sensor assembly 74 may be preferably mounted on and at least partially exposed location on the first housing 50 facing a frontal portion of the toilet bowl 100 and be so positioned/oriented to detect the presence of an individual utilizing the toilet bowl 100. The sensor assembly 74 may be further structured to activate the fan assembly 60 while an individual remains in a predetermined detection zone, associated with the use of the toilet bowl 100. Automatic shutoff of the fan assembly 60 will result upon an absence of an individual from the aforementioned detection zone. Powering of the fan assembly 60 may best be accomplished by the direct wired connection 112 to the conventional AC power source, typically associated with most commercial locations, which include restrooms and or semi-public toilet facilities. Interconnection of the fan assembly 60, sensor assembly 74, one or more light units 72 and other electrically powered structures of the filter assembly 10' may be accomplished by appropriate control circuitry such as, but not limited to, printed circuitry 24, as described above with reference to the filtering assembly 10.

As a possible additive feature, a fragrance scent dispensing device or structure 40' may be included within the interior of the first housing 50 similar to the fragrance or scent dispensing structure 40 of the embodiment of FIGS. 4B and 4C.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An assembly for filtering odors from a commercial toilet bowl comprising:
   a first housing disposed in spaced relation to the commercial toilet bowl and including a filter assembly,
   a second housing adjacent the commercial toilet bowl and including an inlet disposed in fluid communicating relation with an interior of the commercial toilet bowl,
   said first housing disposed vertically above said second housing and the commercial toilet bowl in supported attachment to a supportive wall,
   said second housing and said inlet disposed in supported attachment to a plumbing fixture, above and rearwardly of the commercial toilet bowl and a toilet seat thereon,
   a conduit extending vertically upward from said second housing to said first housing along and in adjacent relation to the supportive wall; said conduit disposed in interconnecting, fluid communicating relation between interiors of said first and second housings,
   a fan assembly mounted within said first housing in fluid communicating relation with said conduit,
   said fan assembly disposed to direct fluid flow from said conduit through said interior of said first housing and outwardly therefrom to an exterior of said first housing, and
   wherein activation of said fan assembly defining a path of fluid flow extending from the commercial toilet bowl, into said inlet, through said second housing and along said conduit into said first housing and through said filter assembly, to the exterior of said first housing.

2. The assembly as recited in claim 1 wherein said filter assembly includes a first filter unit structured to process odor in fluid passing therethrough.

3. The assembly as recited in claim 2 wherein said first filter unit comprises a carbon-based filter.

4. The assembly as recited in claim 2 wherein said filter assembly further comprises a second filter unit structured to process particulates in aerosolized fluid passing therethrough.

5. The assembly as recited in claim 4 wherein said second filter unit comprises a HEPA filter.

6. The assembly as recited in claim 4 further comprising a fluid sterilizing assembly disposed within said first housing, downstream of said conduit and upstream of said fan assembly.

7. The assembly as recited in claim 6 wherein said fluid sterilizing assembly comprises a plurality of UV light units disposed in vertically spaced relation to one another and collectively disposed in a transverse orientation relative to said path of fluid flow.

8. The assembly as recited in claim 7 wherein said first filter unit, said second filter unit and said fluid sterilizing assembly are disposed within said path of fluid flow.

9. The assembly as recited in claim 1 further comprising a fluid sterilizing assembly, including at least one UV light unit, disposed within said first housing in a transverse orientation relative to said path of fluid flow and downstream of said conduit and upstream of said fan assembly.

10. The assembly as recited in claim 1 further comprising a sensor assembly mounted on said first housing and structured and disposed to determine the use of the commercial toilet bowl by an individual; said sensor assembly connected in activating relation to said fan assembly.

11. The assembly as recited in claim 10 wherein said sensor assembly comprises a motion sensor.

12. The assembly as recited in claim 10 wherein said first housing and said sensor assembly face outwardly from the supportive wall for said first housing, in an exposed relation to a substantially frontal portion of the commercial toilet bowl.

* * * * *